United States Patent
Grindlay Lledó et al.

(10) Patent No.: US 12,118,710 B2
(45) Date of Patent: Oct. 15, 2024

(54) PROCESS FOR THE DETECTION OF BITTER ALMONDS BASED ON THE PROCESSING OF DIGITAL IMAGES AND A DEVICE ASSOCIATED THEREWITH

(71) Applicant: UNIVERSITAT D'ALACANT/UNIVERSIDAD DE ALICANTE, San Vicente del Raspeig (ES)

(72) Inventors: Guillermo Grindlay Lledó, San Vicente del Raspeig (ES); Luis Gras Garcia, San Vicente del Raspeig (ES); Juan Mora Pastor, San Vicente del Raspeig (ES); Marta Navas García, San Vicente del Raspeig (ES)

(73) Assignee: UNIVERSITAT D'ALACANT/UNIVERSIDAD DE ALICANTE, San Vicente del Raspeig (ES)

( * ) Notice: Subject to any disclaimer, the term of this patent is extended or adjusted under 35 U.S.C. 154(b) by 371 days.

(21) Appl. No.: 17/506,718

(22) Filed: Oct. 21, 2021

(65) Prior Publication Data
US 2022/0044392 A1    Feb. 10, 2022

Related U.S. Application Data

(63) Continuation-in-part of application No. PCT/EP2020/025293, filed on Jun. 19, 2020.

(30) Foreign Application Priority Data

Jun. 20, 2019  (ES) .................................. 201930561

(51) Int. Cl.
G06T 7/90    (2017.01)
G06T 7/00    (2017.01)
G06T 7/10    (2017.01)

(52) U.S. Cl.
CPC .............. *G06T 7/0008* (2013.01); *G06T 7/10* (2017.01); *G06T 7/90* (2017.01); *G06T 2207/10064* (2013.01); *G06T 2207/30128* (2013.01)

(58) Field of Classification Search
CPC ........... G06T 7/0008; G06T 7/10; G06T 7/90; G06T 2207/10064; G06T 2207/30128
See application file for complete search history.

(56) References Cited

U.S. PATENT DOCUMENTS

| | | | |
|---|---|---|---|
| 2012/0093985 A1* | 4/2012 | Vasilescu | G06T 7/0004 382/110 |
| 2016/0207071 A1* | 7/2016 | Cohn | G01N 21/8901 |

OTHER PUBLICATIONS

Victoria Cortés, Discrimination of intact almonds according to their bitterness and prediction of amygdalin concentration by Fourier transform infrared spectroscopy, Nov. 18, 2018, pp. 236-24s (Year: 2018).*

* cited by examiner

*Primary Examiner* — Ian L Lemieux
*Assistant Examiner* — Sebastian-Sy Vuchi Ngo
(74) *Attorney, Agent, or Firm* — Farber LLC; Jonathan Winter

(57) ABSTRACT

Procedure for the detection of bitter almonds based on the processing of digital images, and a system and device associated therewith. Detection procedure and system for the automated classification of sweet and bitter almonds based on the processing of digital images. The fluorescence of the cyanogenic compounds naturally present in almonds generates a clear difference in colour between sweet and bitter almonds which subsequently is analysed and classified by means of a computer program. The invention also includes the device, either portable or automatic, for carrying out the classification of bitter or sweet almonds. This (Continued)

device will be necessary during the goods reception process and in the validation/verification of the quality of the finished product, prior to the loading and transport process.

20 Claims, 8 Drawing Sheets

PROCESS FOR THE DETECTION OF BITTER ALMONDS BASED ON THE PROCESSING OF DIGITAL IMAGES AND A DEVICE ASSOCIATED THEREWITH

CROSS-REFERENCE TO RELATED APPLICATIONS

This application is filed under the provisions of 35 U.S.C. § 111(a) and is a continuation-in-part of International Patent Application No. PCT/EP2020/025293, filed on 19 Jun. 2020 entitled "PROCESS FOR THE DETECTION OF BITTER ALMONDS BASED ON THE PROCESSING OF DIGITAL IMAGES AND A DEVICE ASSOCIATED THEREWITH" in the name of Guillermo GRINDLAY LLEDÓ, which claims priority to Spanish Patent Application No. P201930561 filed on 20 Jun. 2019, both of which are hereby incorporated by reference herein in their entirety.

FIELD OF THE INVENTION

The present invention falls within the field of the identification of bitter almonds, and relates specifically to a new procedure, and to a system and a device associated therewith, to discriminate between bitter almonds and sweet almonds.

STATE OF THE PRIOR ART

The almond tree is a vegetal species with great genetic variability. This genetic wealth has enabled it to adapt to highly varied environmental conditions. The bitter or sweet (non-bitter) taste is a monogenic trait, sweet being dominant, although bitter almonds still have a considerable presence in Spanish crops. The bitter taste of the almond is due to the presence in its composition of cyanogenic glycosides (amygdalin, prunasin, etc.), which have the capability of degrading in the presence of specific enzymes, producing benzaldehyde and hydrocyanic acid. This process is known as cyanogenesis. In the case of the almond, the specific compound is amygdalin, and the enzyme is the amylase present in saliva.

According to the Spanish Ministry of Agriculture, Fisheries, Food and the Environment (MAPAMA), the USA, specifically California, is the absolute leader in the world production of almonds, with 80% of the market share; followed at a great distance by Australia (8%) and Spain (5%). These three countries represent 93% of world production. Australian and European production is growing, while the growth forecast for California for the coming years is expected to be minimal, due to drought and to the increase in plantations of other nuts, such as pistachio nuts.

The USA markets almond varieties of a standardised quality which, although their organoleptic characteristics are greatly inferior to the Mediterranean varieties, are not handicapped by bitterness which is, in fact, their greatest selling point: they are suppliers of a "non-toxic", bitterless product.

Spain is a great worldwide importer of almonds. The American almond is used to supply Spanish industry, and once processed it is exported, mainly to Germany, France and Italy.

Therefore, the presence of a small percentage of bitter almonds in shipments of sweet almonds has significant economic repercussions for the producers of almonds and their derivatives, due to the loss of organoleptic quality and the possible toxicity of the product. Therefore, determining the presence of a bitter almond in a rapid, simple, non-destructive way, prior to placing the product on the market, is of vital importance for manufacturers in the sector.

The distrust by the secondary processing industry, the manufacturers of products and by-products containing almonds, with regard to the primary industry, the almond producers and harvesters, is enormous. There is currently no discriminative method which fulfils all the requirements of the sector and which can be implemented in production facilities, such that both groups therefore repeat the same subjective process of random sampling at their facilities, and the result is well known: mass returns of shipments and recourse to imports.

Conventional methods for the detection of bitter almonds are based on qualitative and quantitative techniques. The most widely used in qualitative terms is sensory analysis, as explained in the article by G. V. Civille, K. Lapsley, G. Huang, S. Yada, J. Seltsam "Development of an almond lexicon to assess the sensory properties of almond varieties", where the person in charge of product reception randomly samples several almonds in order to establish the percentage relationship between bitter and sweet almonds, and therefore to accept or reject the goods. This determination is totally subjective, such that on many occasions discrepancies in the results may arise, depending on the sensitivity of the operator's palate. The most widely used quantitative method is the High-Performance Liquid Chromatography (HPLC) technique, explained in the article by M. Padilla, M. Monserrath, T. Oliag, L. Garcia, M. Jesus, C. López "Almendras dulces y amargas: determinación del contenido de Amigdalina mediante cromatografía liquida de alta resolución y clasificación mediante espectroscopia visible y de infrarrojo cercano." ("Sweet and bitter almonds: the determination of Amygdalin content by high-performance liquid chromatography and classification by visible and near-infrared spectroscopy"). This technique requires the use of sophisticated, high-cost instrumentation, in addition to operation by a highly-qualified operator, and wherein, in addition, the chromatographic development necessary to obtain the results requires a period of time that may vary around thirty minutes or longer, depending on the experimental conditions employed.

Simpler qualitative options exist for the detection of bitter almonds, such as the use of thin-layer chromatography or the utilization of commercial test kits. However, these require the use of highly toxic or even carcinogenic reagents such that their use is not recommended except under certain safety conditions.

Other novel techniques which seek to classify almonds by non-destructive, visual techniques and with image processing are the cases of N. Teimouri, M. Omid, K. Mollazade, A. Rajabipour "An Artificial Neural Network-Based Method to Identify Five Classes of Almond According to Visual Features" and T. Pearson, R. Young "Automated sorting of almonds with embedded shell by laser transmittance imaging", where they seek to identify, according to their shape, colour and texture, the broken/cracked units, the double almonds and the pieces of shell that may remain in the product after shelling, in large batches of almonds. However, in this case the technical problem resolved is different, given that it consists of eliminating the almond shells, which are detected based on the oil content, this being high in the nut and null in the shell, by capturing images of the light transmitted through the nucleus.

Other techniques which may be useful are visible (VIS) spectroscopy and near-infrared (NIR) spectroscopy which, in combination with Raman techniques, are used to differentiate sweet and bitter almonds. However, in this case, specific positioning of the almond in the classification cell is essential, this entailing an added difficulty, in addition to the time required for detection and the complexity and cost of said techniques.

A related example is patent ES2684855 A1, which protects an inspection procedure and equipment which discriminates between sweet and bitter almonds by means of vibrational spectroscopic techniques, more specifically NIR. This technique is already used to determine concentrations of amygdalin, but it is not recommended for concentrations lower than 3% due to its lack of specificity and surface irregularities in the sample. Besides, another drawback of this patent is that it requires an optimal positioning of the almond in the cell, that is, it must be totally centred with the NIR detector/sensor, otherwise there is the risk that the light beam is positioned on one extremity of the almond and incorrect results are obtained. This fact impedes the industrial in-line adaptation thereof, and the sampling of 100% of the product, as the speeds required in industries do not allow the positioning of the almonds one by one. Furthermore, the processing of the data of the NIR spectrum is not immediate, requiring a certain amount of time, for which reason it also would not be suitable for implementation of real-time detection systems.

The characteristics of the company staff and the speed and precision required in the analyses entail that these techniques are neither optimal nor operative in the business world. In contrast, the development and adaptation of in-line analytical methods is required in order to be able to simply, rapidly and reliably discriminate between sweet and bitter almonds in real situations.

Another patent which makes reference to the determination of food quality parameters by means of the capture and analysis of digital images is WO 2014/053679 A1. In said patent, by means of the processing of ocular images of a fish eye and a computer programme, the quality and freshness of the fish is determined by interpolating the values of CIEL*a*b* parameters. L*a*b* is the international standard for the measurement of colour, adapted by the International Commission on Illumination (CIE), although other colour spaces do exist, the most widely used of these in the measurement of colour in foodstuffs is the L*a*b* colour space, due to the fact that a uniform distribution of colours is obtained and it is very close to the human perception of colour. In this case, the classification is performed based on the outline of the eye of the fish and the identification of the centre of the pupil. The shape of the eye of the fish varies over time from the moment of its capture, and this variation in shape is subsequently correlated with the freshness of the product. US2012/093985 A1 relates to a system and method for aflatoxin detection in produce based on red-orange fluorescence, while US2012/061586 A1 relates to a system and method for fluorescence spectral imaging of target material to detect the presence of a contaminant such as aflatoxin in corn, and U.S. Pat. No. 4,535,248 relates to a method for detecting aflatoxin in almonds. On the other hand, CN109320438A relates to a naphthalene-based fluorescent probe for detecting cyanide in food and a method of synthesis and use thereof. Systems and methods for automatic inspection and external and internal quality evaluation of fruits and vegetables are reviewed in *Food Bioprocess Technol.* (2011) 4:487-504.

The present invention is not based on the determination and classification of foodstuffs according to their two-dimensional shape, as the patent WO 2014/053679 A1 shows, since numerous varieties of almonds exist, and each takes on different dimensions. The most widely marketed is the "common" almond, which includes mixtures of different varieties and sizes, at a competitive price. In this way, our invention is based on classification as a function of the difference in colour generated by different compounds among samples, and not their shape or size. Cyanogenic compounds are present in large quantities in bitter almonds, this not being the case with sweet almonds.

To date, the analytical methods available for the detection of bitter almonds do not fulfil the requirements demanded by companies in the sector: economy, simplicity, rapidity, reliability, the handling of toxic substances and ease of operation by personnel with no specific technical training. In view of the solutions and precedents existing in the state of the art, a procedure and a device are required to solve the problem of the detection of bitter almonds.

BRIEF DESCRIPTION OF THE INVENTION

The present invention relates to a procedure for the detection of bitter almonds, which comprises the following stages:
(a) Placing at least one almond on a surface by means of a manual or automatic supply system;
(b) Illuminating the almond with a source of ultraviolet (UV) radiation;
(c) Acquiring an image of the almond with a photographic camera and storing said image in an internal or external system for subsequent analysis;
(d) Processing said acquired image with a computer system that comprises a programme for applying a discriminative model;
(e) Classifying the almond according to the discriminative model of stage (d); and
(f) Withdrawing the almond by means of a manual or automatic withdrawal system.

The present invention also relates to a system for the detection of bitter almonds, which comprises the following:
(a) means for placing at least one almond on a surface by means of a manual or automatic supply system;
(b) means for illuminating the almond with a source of ultraviolet (UV) radiation;
(c) means for acquiring an image of the almond with a photographic camera and storing said image in an internal or external system for subsequent analysis;
(d) means for processing said acquired image with a computer system that comprises a programme for applying a discriminative model;
(e) means for classifying the almond according to the discriminative model of (d); and means for withdrawing the almond by means of a manual or automatic withdrawal system.

The present invention additionally relates to a device for the detection of bitter almonds which comprises at least:
A cell where the sample to be analysed is positioned.
A UV light radiation system with at least one source of UV light.
A positioned photographic camera which photographs the sample for subsequent analysis by means of the computer system.
A computer system which comprises a programme for classification of the sample into sweet and bitter almonds depending on the result obtained upon applying the discriminative model.

Moreover, the present invention relates to a procedure for the detection of bitter almonds, which comprises the following stages:

(a) placing at least one skinned almond on a surface by means of a manual or automatic supply system;
(b) illuminating the almond with a source of ultraviolet (UV) radiation;
(c) acquiring an image of the almond with a photographic camera and storing said image in an internal or external system for subsequent analysis;
(d) processing said acquired image with a computer system that comprises a programme for applying a discriminative model by:
  (i) segmenting the image into RGB channels and obtaining the average RGB values over all pixels of said image;
  (ii) transforming the average RGB values into the corresponding L*a*b* values;
  (iii) interpolating:
    a value Va from the discriminative model using the L* and a* values of said almond when said discriminative model is a combination of the L* and a* values of each member of a population comprising bitter almonds and non-bitter almonds, wherein said combination discriminates between the sub-population of bitter almonds and the sub-population of non-bitter almonds in said population, wherein bitter almonds are assigned to a range Ra1 of said combination and non-bitter almonds are assigned to a range Ra2 of said combination; or
    a value Vb from the discriminative model using the L* and b* values of said almond, when said discriminative model is a combination of the L* and b* values of each member of said population, wherein said combination discriminates between the sub-population of bitter almonds and the sub-population of non-bitter almonds in said population, wherein bitter almonds are assigned to a range Rb1 of said combination and non-bitter almonds are assigned to a range Rb2 of said combination; and
(e) classifying the almond using the value Va or Vb obtained according to the discriminative model of step (d), wherein said almond is classified as a bitter almond when:
  Va falls inside range Ra1;
  Va falls outside range Ra2;
  Vb falls inside range Rb1; or
  Vb falls outside range Rb2; and
(f) optionally withdrawing the sample by means of a manual or automatic withdrawal system.

Furthermore, the present invention relates to a system for the detection of bitter almonds, which comprises the following:
(a) means for placing at least one skinned almond on a surface by means of a manual or automatic supply system;
(b) means for illuminating the almond with a source of ultraviolet (UV) radiation;
(c) means for acquiring an image of the almond with a photographic camera and storing said image in an internal or external system for subsequent analysis;
(d) means for processing said acquired image with a computer system that comprises a programme for applying a discriminative model by:
  (i) segmenting the image into RGB channels and obtaining the average RGB values over all pixels of said image;
  (ii) transforming the average RGB values into the corresponding L*a*b* values;
  (iii) interpolating:
    a value Va from the discriminative model using the L* and a* values of said almond when said discriminative model is a combination of the L* and a* values of each member of a population comprising bitter almonds and non-bitter almonds, wherein said combination discriminates between the sub-population of bitter almonds and the sub-population of non-bitter almonds in said population, wherein bitter almonds are assigned to a range Ra1 of said combination and non-bitter almonds are assigned to a range Ra2 of said combination; or
    a value Vb from the discriminative model using the L* and b* values of said almond, when said discriminative model is a combination of the L* and b* values of each member of said population, wherein said combination discriminates between the sub-population of bitter almonds and the sub-population of non-bitter almonds in said population, wherein bitter almonds are assigned to a range Rb1 of said combination and non-bitter almonds are assigned to a range Rb2 of said combination; and
(e) means for classifying the almond using the value Va or Vb obtained according to the discriminative model of (d), wherein said almond is classified as a bitter almond when:
  Va falls inside range Ra1;
  Va falls outside range Ra2;
  Vb falls inside range Rb1; or
  Vb falls outside range Rb2; and
(f) optionally, means for withdrawing the sample by means of a manual or automatic withdrawal system.

EXPLANATION OF THE INVENTION

The present invention relates to a procedure and system that each permit the rapid classification of almonds without use of a panel of trained tasters nor instrumental methods. The procedure and system each permit the classification to be performed based exclusively on the processing of different parameters of digital images which are compared with a system for the storage of analysed and processed data. The procedure and system each permit the generation and storage of discriminative models in order to automatically be able to differentiate bitter almonds.

The present invention, in a first aspect, relates to a procedure for the detection of bitter almonds which comprises the following stages:
a) Placing at least one sample on a surface by means of a manual or automatic supply system.
b) Illuminating the sample with a source of ultraviolet (UV) radiation.
c) Photographing the sample with a photographic camera and storing said photograph (i.e. acquiring an image of the almond with a photographic camera and storing said photograph image) in an internal or external system for subsequent analysis.
d) Processing said acquired image with a computer system that includes a programme for applying a discriminative model.
e) Classifying the sample according to the discriminative model of the previous stage.

f) Withdrawing the sample by means of a manual or automatic withdrawal system.

Stage (d), which carries out processing of the image, in turn comprises the following stages:
1. Processing the data of the acquired image and segmentation of the image to establish the RGB colour parameter or parameters of the sample.
2. Transforming the photographic parameters obtained in the previous RGB stage (i.e. the RGB colour parameters obtained in the previous stage) into at least one L*a*b* parameter of the CIEL*a*b* space.
3. Determining at least one of the L*, a* and/or b* parameters of the CIEL*a*b* space and its corresponding value in the image.
4. Interpolating the value obtained in stage 3 in at least one discriminative model based on the values obtained with different sample types of sweet and bitter almonds acquired under said predetermined conditions.

Analogously, the present invention, in a second aspect, also relates to a system for the detection of bitter almonds, which comprises the following:
(a) means for placing at least one almond on a surface by means of a manual or automatic supply system;
(b) means for illuminating the almond with a source of ultraviolet (UV) radiation;
(c) means for acquiring an image of the almond with a photographic camera and storing said image in an internal or external system for subsequent analysis;
(d) means for processing said acquired image with a computer system that comprises a programme for applying a discriminative model;
(e) means for classifying the almond according to the discriminative model of (d); and
(f) means for withdrawing the almond by means of a manual or automatic withdrawal system.

In a preferred embodiment of the system for the detection of bitter almonds of the present invention (d) in turn comprises the following:
i. means for processing the data of the acquired image and segmentation of the image to establish the RGB colour parameters of the sample;
ii. means for transforming the RGB colour parameters obtained in stage i into at least one L*a*b* parameter of the CIE L*a*b* space;
iii. means for determining at least one of the L*, a* and/or b* parameters of the CIE L*a*b* space and its corresponding value in said image; and
iv. means for interpolating the value obtained by iii in a minimum of one discriminative model generated from the values obtained with different sample types acquired under said predetermined conditions.

In the procedure and system of the present invention, the sample is an almond. Each almond is an almond that has been removed from its shell, and is preferably a peeled (i.e. skinned or blanched) almond.

In a particular embodiment of the procedure and system of the present invention, the sample is placed in a closed cell without penetration of sunlight.

In a particular embodiment of the procedure and system of the present invention, the illumination of the cell is carried out with UV radiation having wavelengths<400 nm at a distance between the light source and the sample of between 0.1 m and 1 m. Said distance must be sufficiently close for said light to shine on the surface of the sample and generate a significant difference in colour according to the type of almond.

In a particular embodiment of the procedure and system of the present invention, the photography of the sample is performed at a distance between the camera and the sample of between 0.1 m and 1 m, under conditions of the absence of sunlight and application of UV radiation. Said distance should be optimal for photographing the sample, and will be defined by the size of the sample, the power of the camera and the source of UV radiation.

In a particular embodiment of the procedure and system of the present invention, the procedure comprises an intermediate stage between (a) and (b) for the homogenous (i.e. even) distribution of the samples, which may be carried out in a more preferred embodiment of the procedure and system of the present invention, for example, by means of vibrating conveyor belts or tables.

The supply or dispensing of the almond to the surface or cell may be performed manually or automatically, individually or in batches, by means of a hopper or conveyor belt adapted to the line, that supplies almonds in an ordered manner to said surface or cell.

In the present invention it is not necessary to individually classify the almonds, several almonds may be classified simultaneously, the only requirement being that the almonds are not piled one on top of the other in order to optimise the procedure. This is achieved by including the aforementioned intermediate stage for the homogenous distribution of the samples.

Subsequent to placing of the almonds, the UV radiation system generates clear and automatic differentiation in the colour of the sweet almonds and bitter almonds. This difference in colour between the two is based on the fluorescence of the cyanogenic compounds naturally present in the almonds.

Subsequently, the camera takes a photograph wherein it measures and determines the R, G, B parameters in the image, with which it is possible to represent a colour by means of the additive mix of the three primary colours of light: red, green and blue. These values may vary depending on the device with which they are processed, therefore, by means of the computer programme or application, they are translated to L*, a*, b* values, also known as CIEL*a*b*. This consists of three channels, where L* is the luminosity and a* and b* are the chromatic coordinates (a*=red/green coordinates (+a indicates red, −a indicates green) and b*=yellow/blue coordinates (+b indicates yellow, −b indicates blue)). Upon creating scales for these attributes, we can precisely express the colour, irrespective of the subjective perception and interpretation. The interpolation of said values is associated with a discriminative model and calibration curve generated from the values previously obtained with almonds of different varieties under the same predetermined conditions. This prior discriminative model serves to classify the units as "bitter" and "non-bitter" almond.

In a preferred embodiment of the procedure and system for the detection of bitter almonds of the present invention:
(A) said almond is a skinned almond;
(B) (d) in turn comprises the following:
(i) segmenting the image into RGB channels and obtaining the average RGB values over all pixels of said image;
(ii) transforming the average RGB values into the corresponding CIE L*a*b* values;
(iii) interpolating:
a value Va from the discriminative model using the L* and a* values of said almond when said discriminative model is a combination of the L* and a* values of each member of a population comprising bitter almonds and non-bitter almonds, wherein said combination discriminates between the sub-population of bitter almonds and the sub-population of non-bitter almonds in said population, wherein bitter almonds are assigned to a range Ra1 of said combination and non-bitter almonds are assigned to a range Ra2 of said combination; or a value Vb from the discriminative model using the L* and b* values of said almond, when said discriminative model is a combination of the L* and b* values of each member of said population, wherein said combination discriminates between the sub-population of bitter almonds and the sub-population of non-bitter almonds in said population, wherein bitter almonds are assigned to a range Rb1 of said combination and non-bitter almonds are assigned to a range Rb2 of said combination; and (C) (e) classifies the almond using the value Va or Vb obtained according to the discriminative model of (d), wherein said almond is classified as a bitter almond when:

Va falls inside range Ra1;
Va falls outside range Ra2;
Vb falls inside range Rb1; or
Vb falls outside range Rb2.

In a more preferred embodiment of the procedure and system for the detection of bitter almonds of the present invention, said discriminative model is developed by:

(I) performing (a) to (c) for each almond in said population comprising bitter almonds and non-bitter almonds;
(II) segmenting each image acquired for each almond in said population into RGB channels and obtaining the average RGB values over all pixels of each image;
(III) transforming the average RGB values of each image acquired for each almond in said population into the corresponding CIE L*a*b* values;
(IV) calculating a combination of:
  the L* and a* values of each almond in said population; or
  the L* and b* values of each almond in said population
wherein each combination discriminates between the sub-population of bitter almonds and the sub-population of non-bitter almonds in said population.

An even more preferred embodiment of the procedure and system for the detection of bitter almonds of the present invention additionally comprises the following after (III) and before (IV), of performing multivariate data analysis by linear discriminant analysis which obtains:

a discriminant function when using the R, G and B parameters of each almond in said population; or
a discriminant function when using L*, a* and b* parameters of each almond in said population, wherein:
the value of the discriminant function determined using the R, G and/or B parameters of each almond in said population; or
the value of the discriminant function determined using the L*, a* and/or b* parameters of each almond in said population
discriminates between the sub-population of bitter almonds and the sub-population of non-bitter almonds in said population.

In the present invention, the population used for developing the discriminative model preferably comprises n bitter almonds and m non-bitter almonds, wherein n and m are independently selected from the set of whole numbers greater than or equal to 2, more preferably the set of whole numbers greater than or equal to 10, even more preferably the set of whole numbers greater than or equal to 50, ans still more preferably the set of whole numbers greater than or equal to 100. In one embodiment, n=m.

For the purposes of the invention, each image of the almond is considered only to comprise pixels that represent that of one almond without any pixels that represent other elements such as the background. Accordingly, it is possible to acquire an image of multiple almonds using the photographic camera and to identify the pixels representing each almond therein using image recognition software such as "perClass Mira" based on Artificial Intelligence (e.g. neural networks). In this manner, an image is acquired of each individual almond and the information in the pixels representing any given almond are those which are subjected to processing in order to classify said almond. Thus, in a preferred embodiment of the procedure and system for the detection of bitter almonds of the present invention, (c) comprises acquiring an image of multiple almonds, wherein each image of each almond is separated therefrom by image recognition software.

Thus, in a preferred embodiment of the system according to the present invention:

the means for placing at least one skinned almond on a surface comprises a manual or automatic supply or dispensing means;
the means for illuminating the almond with a source of ultraviolet (UV) radiation comprises a cell where the sample to be analysed is positioned and a UV light radiation system with at least one source of UV light;
the means for acquiring an image of the almond comprises a positioned photographic camera which photographs the sample for subsequent analysis by means of the computer system; and
the means for processing said acquired image comprises a computer system which comprises a programme for applying a discriminative model for classification of the sample into sweet and bitter almonds depending on the result obtained upon applying the discriminative model.

The computer system may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may include, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices or systems from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the procedure of the present invention, and in the system and device of the present invention, may be coded information in the form of assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the users computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams (see FIGS. 5 to 8) of the procedure and system of the present invention which are implemented in the optical communication device and optical communication transmitter. It will be understood that each square or diamond-shaped block of the flowchart illustrations and/or block diagrams, and combinations of blocks in the flowchart illustrations and/or block diagrams, can be implemented by mechanical means, optical techniques or computer readable program instructions, or combinations thereof.

These computer readable program instructions may be provided to a processor of a general-purpose computer, special purpose computer, or other programmable data processing apparatus to produce a machine, such that the instructions, which execute via the processor of the computer system or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto the aforementioned microprocessor, a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in FIGS. 5 to 8 illustrate the architecture, functionality, and operation of possible implementations of methods, systems and devices according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in FIG. 5 or 6. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, once the detection of the bitter almonds has been performed, the sample proceeds to be withdrawn by means of a manual or automatic withdrawal system.

In a third aspect, the present invention relates to a device for carrying out the procedure of the present invention.

In a fourth aspect, the invention relates to a device for the detection of bitter almonds, capable of being adapted in line, which permits classification of bitter and sweet almonds. Specifically, said device comprises at least:

A cell where the sample to be analysed is positioned.

A UV light radiation system with at least one source of UV light.

A photographic camera which photographs the sample for subsequent analysis by means of the computer system.

A computer system which comprises a programme for classification of the sample into sweet and bitter almonds depending on the result obtained upon applying the discriminative model.

In a particular embodiment of the device of the present invention, the cell is closed.

In a particular embodiment of the device of the present invention, the UV light radiation system is located in the upper part of the cell.

In a particular embodiment of the device of the present invention, the photographic camera is located in the upper part of the cell.

In a particular embodiment of the device of the present invention, the UV light radiation system comprises a source of UV light that is applied with wavelengths<400 nm at a distance of between 0.1 m and 1 m between the light source and the sample.

In a particular embodiment of the device of the present invention, the photographic camera is located at a distance of between 0.1 m and 1 m, that photographs the sample in order for it to be subsequently analysed by means of the computer system.

In a particular embodiment of the device of the present invention, the device comprises an activation mechanism.

In a particular embodiment of the device of the present invention, the activation mechanism comprises a button which enables the passage of current.

In a particular embodiment of the device of the present invention, the computer programme controls and processes the detection of bitter almonds, emitting at least one value of the CIEL*a*b* parameters which is compared with the values stored in the image library, permitting its immediate classification on an xy-coordinate graph.

In a particular embodiment of the device of the present invention, the device comprises a vibrating hopper or conveyor belt adapted to the line.

In a particular embodiment of the device of the present invention, the device comprises a manual or automatic sample withdrawal system.

In a particular embodiment of the device of the present invention, the sample withdrawal system comprises air nozzles which are adjustable depending on the positioning of the almond.

The device, procedure and system present a series of highly significant advantages:
1. Simple
2. Rapid
3. Exact
4. Reproducible
5. Non-destructive
6. Automated and in-line industrial implementation
7. Economical
8. Able to be executed by an operator with no specific prior training
9. Based on the principles of green chemistry, fundamentally with regard to the use of reagents, the generation of waste and operator safety. It permits the analysis of the entirety of the almonds without the need for specific positioning, they should only pass through the chamber/cell illuminated with UV radiation and be photographed by the photographic camera.

BRIEF DESCRIPTION OF THE FIGURES

The proposed invention will be more completely understood based on the following detailed description, with reference to the attached figures, which should be considered as illustrative and not limitative, wherein.

DETAILED EXPLANATION OF EMBODIMENT MODES

In the following, a preferred embodiment of the invention is described with reference to the figures accompanying the present document.

The procedure of the first aspect of the invention comprises, as an example of a preferred embodiment, a first stage of capturing a real image of the almonds. In order to take the image, the almonds are placed on the flat surface within the cell with the door 1 closed, in order to achieve appropriate light conditions.

The illumination conditions are determined and optimised by means of an experimental design (ED), assessing the weight and importance of the digital parameters in the differentiation between bitter and sweet almonds. The following are found among said optimised variables: brightness, contrast, hue, saturation, gamma, white balance and exposure. These optimised parameters are comprised between the following values: Brightness (−32-64), Contrast (7-22), Hue (−8000-8000), Saturation (31-94), Gamma (62-185), White balance (4000-5500), Exposure (−1-12).

In order to take the photograph of the almond, specific conditions must be met: distance between the camera and the almonds within an interval of 0.1 m and 1 m, with UV radiation having a wavelength<400 nm and specific photographic parameters. These conditions may be achieved in a closed cell, isolated from sunlight, with no openings at the extremities or sides, manufactured from black or opaque materials, as portrayed in FIGS. 1 and 2. Upon taking the photograph, it is stored.

The processing of the image provides a number of numerical L*a*b* (CIEL*a*b*) values, which permit the correlation of the obtained images and data with the discriminative model. Subsequently, the interpolation of one or more L*a*b* colour parameters obtained with the image of the almonds is carried out in the discriminative model developed with almond samples that were previously classified and quantified by HPLC (high-performance liquid chromatography). Finally, the discriminative model is applied employing software in a MATLAB environment which should be available, either stored in the memory of any portable device or located in a remote online system.

The classification has been performed based on a library of images taken under lighting conditions optimised by means of ED, with a particular camera-almond separation, which should be maintained fixed for all measurements, in order for the result to be correct.

Figure 1:
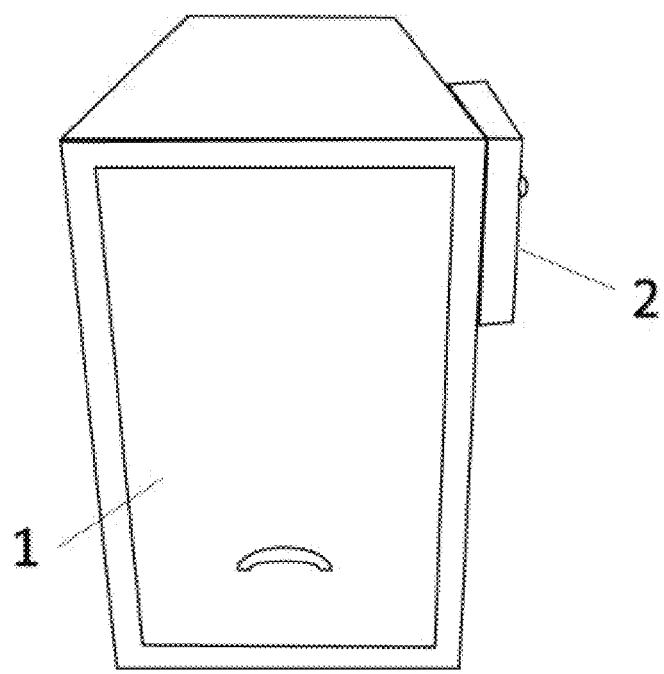
FIG. 1 portrays a front view of the detector device for the classification or differentiation of almonds.
Figure 2:
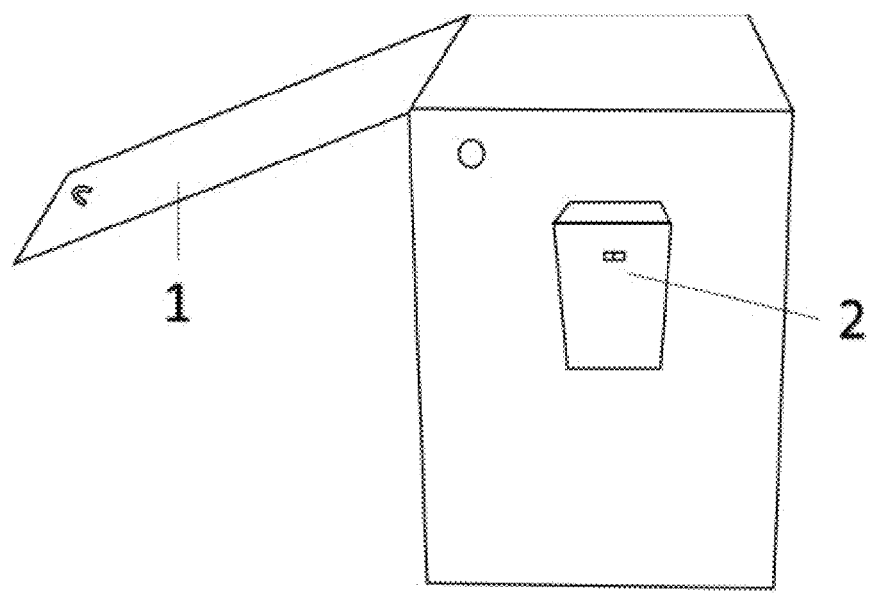
FIG. 2 portrays a lateral perspective view of the almond detector device.

FIG. 1 and FIG. 2 portray the detector device for the differentiation of almonds as a function of the content of cyanogenic compounds present therein.

Figure 4:
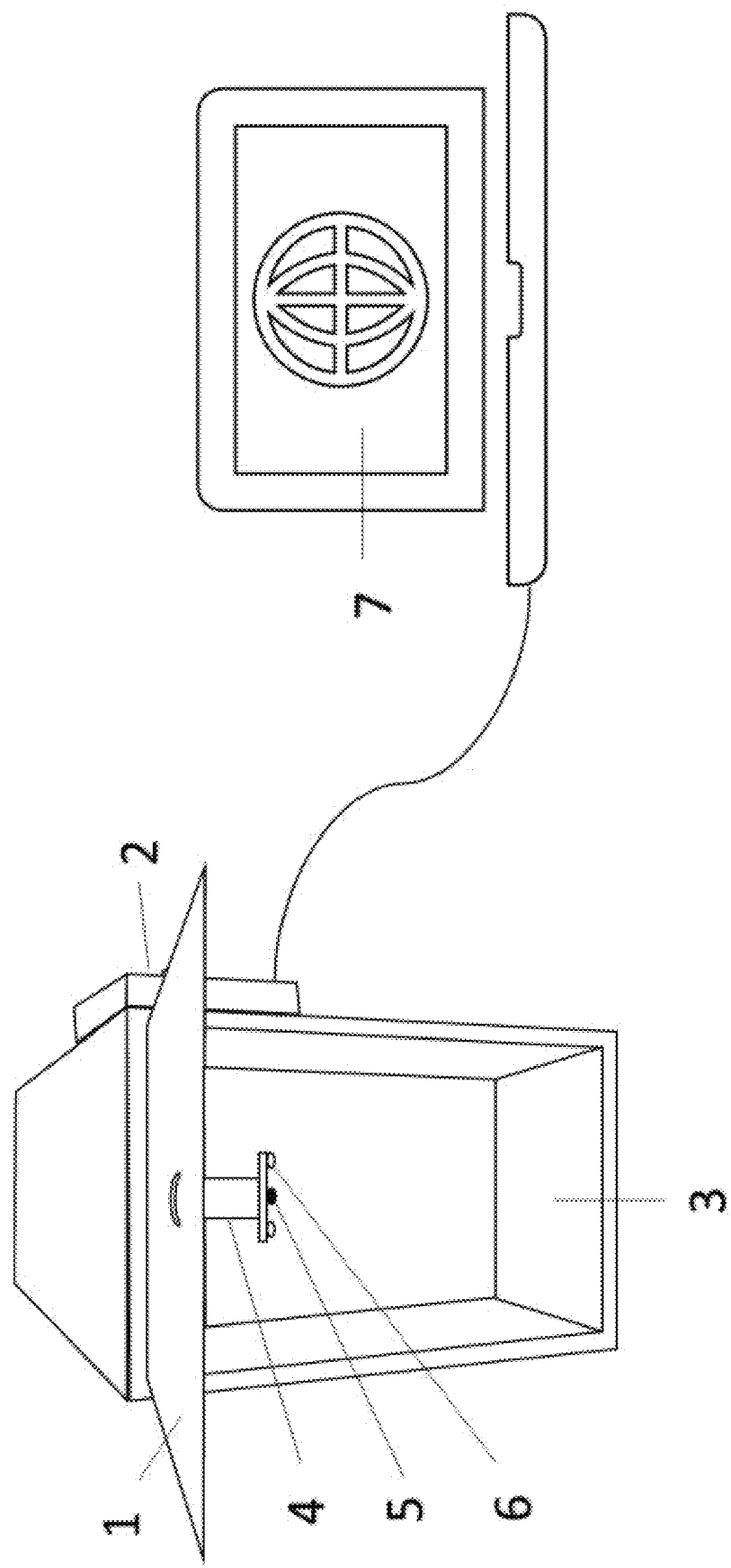
FIG. 4 portrays an interior view of the closed cell where the almonds are introduced and positioned on a flat surface and the device is connected in turn to a computer system which allows processing of the image.
Figure 5:
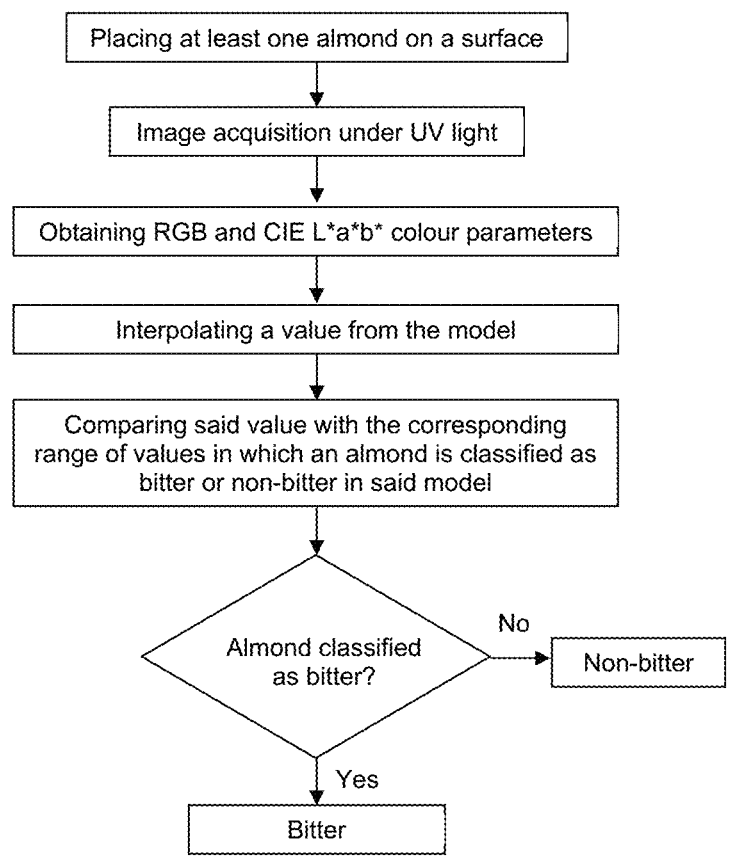
FIG. 5 portrays a flow chart of the classification of bitter almonds according to one embodiment of the present invention.
Figure 6:
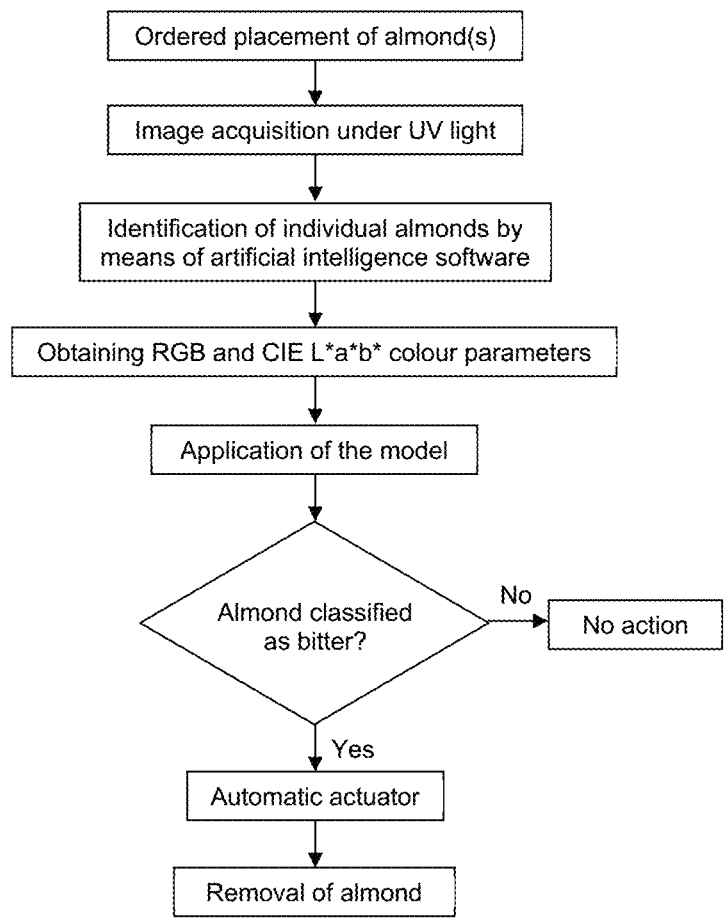
FIG. 6 portrays a flow chart of the classification and elimination of bitter almonds according to a preferred embodiment of the present invention.
Figure 7:
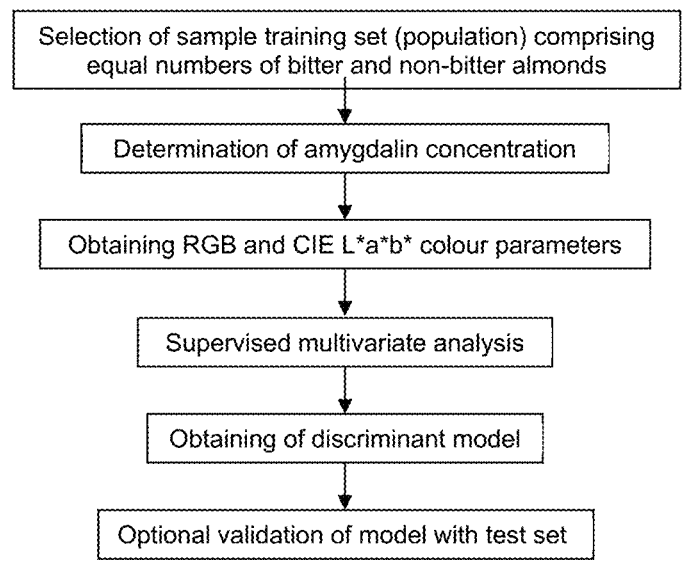
FIG. 7 portrays a flow chart of the development of the discriminative (classification) model used in one embodiment of the present invention.
Figure 8:
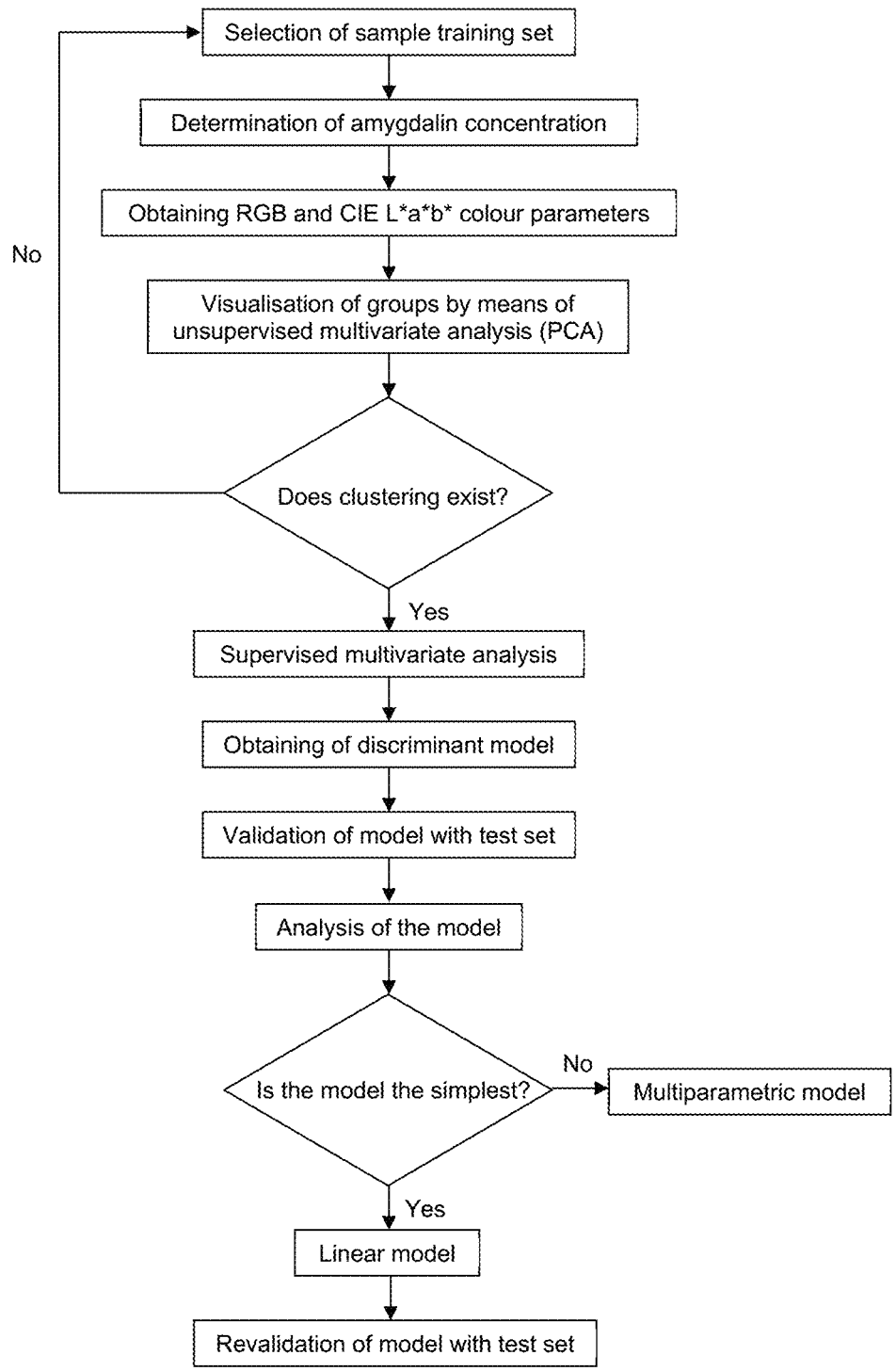
FIG. 8 portrays a flow chart of the development of the discriminative (classification) model used in a preferred embodiment of the present invention.

The almonds are located individually or (non-exclusively) in groups within the cell on the surface 3 of FIG. 4. The door 1 is closed in order to obtain the necessary conditions of absence of sunlight and should remain completely closed while capturing images. In order to capture images we will operate the button 2, which allows the passage of current and activates the UV radiation system and the digital camera 5.

Figure 3:
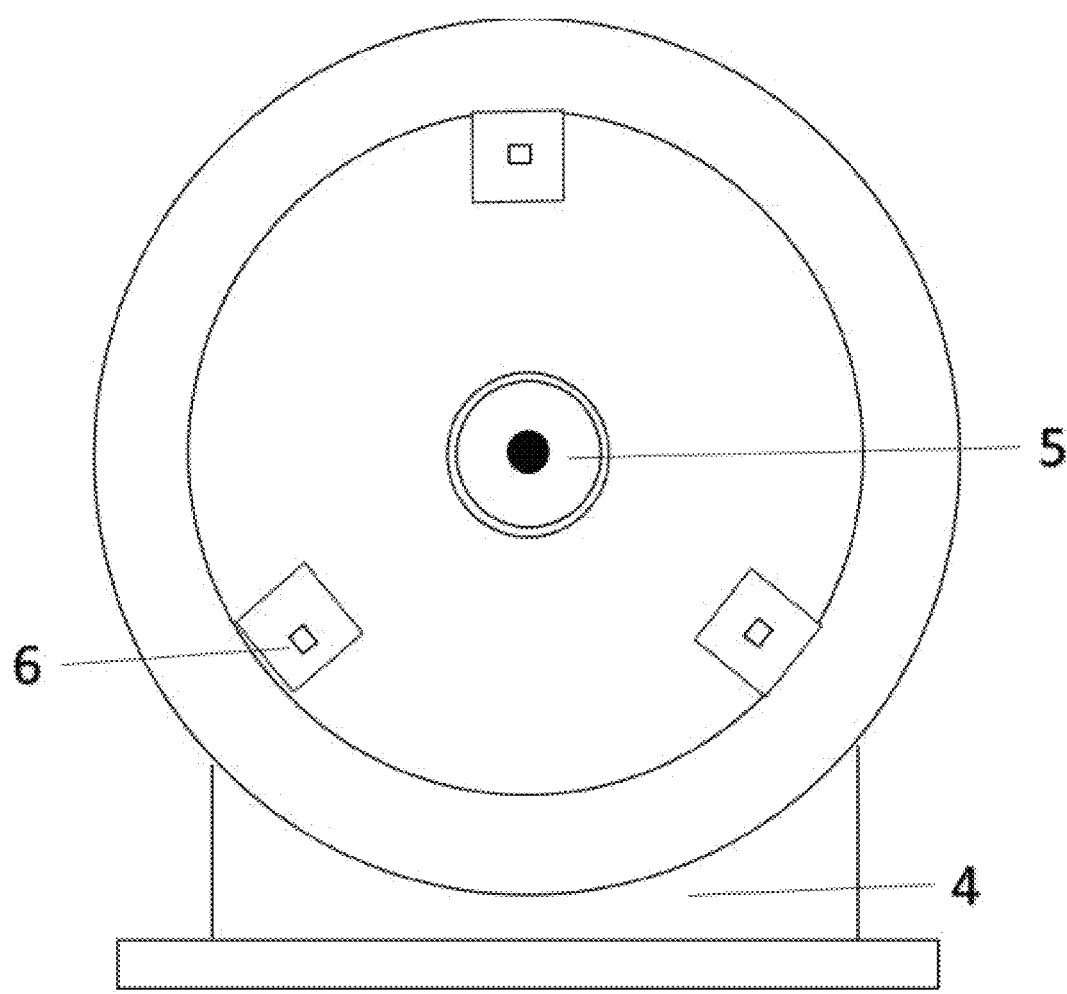
FIG. 3 portrays a detailed view of the integrated radiation system and photographic camera which allow the differentiation of sweet and bitter almonds to take place.

FIG. 3 portrays the integrated digital camera 5 and UV radiation 6 systems required for the capture and analysis of data. Said radiation system 6 consists of at least one source of UV light anchored to the radiation system 4, specifically, in our example the radiation system consists of three sources of UV light. Although the device proposed consists of three UV lights, it is also possible to reduce or increase the number of sources of radiation until sufficient illumination is obtained, as necessary, depending on the height between the almonds and the source of radiation, the internal volume of the cell and the conditions of total or partial absence of sunlight. Thus, the lighting system requires at least one source of radiation, which may be increased in number in order to obtain complete illumination of the entirety of the interior of the cell.

The device should be connected to a computer system 7 with a programme to process the image and to differentiate between bitter and sweet almonds based on at least one colour parameter (R, G, B, L*, a*, b*) of the images obtained.

Example

Model Development:

A model to discriminate between sweet and bitter almonds was developed as follows:

(i) 128 almonds, 64 sweet and 64 bitter almonds were selected. They were divided into two sets, one of 100 almonds (development set: 50 bitter and 50 non-bitter) to develop the model and another of 28 almonds (validation set: 14 bitter and 14 non-bitter) to validate it.

(ii) images were taken at the surface level of all almonds to determine their RGB and, hence, CIE L*a*b* parameters.

(iii) chemical analysis was performed by chromatography of the two sets of almonds in order to determine their composition and thus be certain of the identity (non-bitter/bitter) of each almond.

(iv) an average of the RGB or CIE L*a*b* parameters was made from the image taken of each almond and, through multivariate analysis of the L* and a* or L* and b* parameters of the development set, a linear discriminant model was developed to classify the almonds.

Testing of Model/Classification of Almonds:

Upon interpolating the L* and a* or L* and b* values of each almond in the validation set into the corresponding model, a normalised interpolation value was obtained. If a value of more than 0 is obtained, the almond was classified as bitter. On the contrary, if the value is less than 0, the almond was classified as non-bitter. The goodness of the model was evaluated with the validation set.

Figure 9:
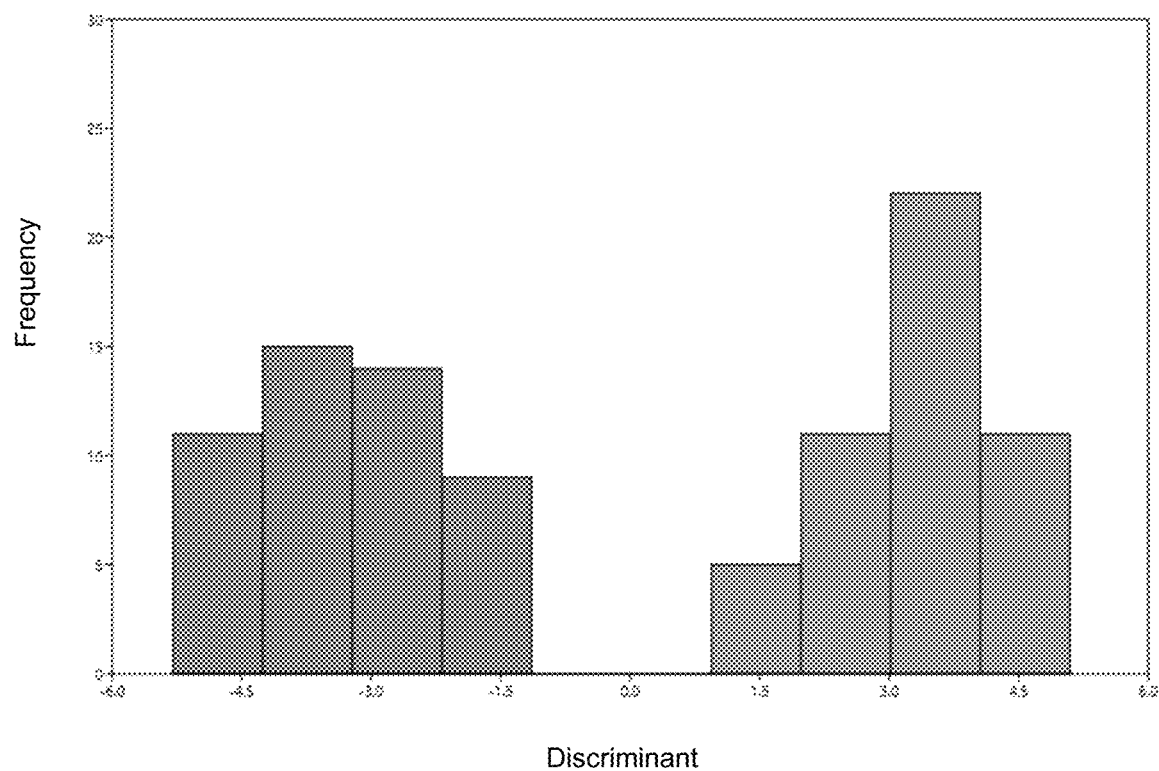
FIG. 9 portrays the results obtained from interpolation of a linear discriminative model which is based on a linear combination of the L* and a* values, according to the present invention, with the corresponding L* and a* values of each almond in said validation set (n=28), wherein almonds having an value which is interpolated from the model that is less than 0 are classified as non-bitter and almonds having a corresponding value that is more than 0 are classified as bitter.

FIG. 9 portrays the validation results obtained by interpolating a discriminative model based on a combination of the L* and a* values with the corresponding L* and a* values of each almond in said validation set. Similar results were obtained by interpolating a discriminative model based on a combination of the L* and b* values with the corresponding L* and b* values of each almond in said validation set. All almonds from the validation set were correctly classified as bitter or non-bitter, with 0% false positives and 0% false negatives using said models.

The invention claimed is:

1. A procedure for the detection of bitter almonds, which comprises the following stages:
    (a) placing at least one almond on a surface by means of a manual or automatic supply system;
    (b) illuminating the almond with a source of ultraviolet (UV) radiation;
    (c) acquiring an image of the almond with a photographic camera and storing said image in an internal or external system for subsequent analysis;
    (d) processing said acquired image with a computer system that comprises a program for applying a discriminative model;
    (e) classifying the almond as bitter or non-bitter according to said discriminative model; and
    (f) withdrawing the almond by means of a manual or automatic withdrawal system, wherein stage (d) in turn comprises the following stages:
    i. processing the data of the acquired image and segmentation of the image to establish the RGB colour parameters of a sample;
    ii. transforming the RGB colour parameters obtained in stage i into at least one L*a*b* parameter of the CIE L*a*b* space;
    iii. determining at least one of the L*, a* and/or b* parameters of the CIE L*a*b* space and its corresponding value in said image; and
    iv. interpolating the value obtained in stage iii in said discriminative model generated from the values obtained with different sample types of bitter and non-bitter almonds acquired under predetermined conditions.

2. The procedure for the detection of bitter almonds according to claim 1, wherein in stage (a), the sample is placed in a closed cell without penetration of sunlight.

3. The procedure for the detection of bitter almonds according to claim 1, wherein the illumination of a cell is carried out with UV radiation having wavelengths<400 nm at a distance between the light source and the sample of between 0.1 m and 1 m.

4. The procedure for the detection of bitter almonds according to claim 1, wherein the photography of the sample is performed at a distance between the camera and the sample of between 0.1 m and 1 m, under conditions of the absence of sunlight and application of UV radiation.

5. The procedure for the detection of bitter almonds according to claim 1,
    wherein:
    said almond is a skinned almond;
    stage (d) in turn comprises the following stages:
    (i) segmenting the image into RGB channels and obtaining the average RGB values over all pixels of said image;
    (ii) transforming the average RGB values into the corresponding CIE L*a*b* values;
    (iii) interpolating:
    a value Va from the discriminative model using the L* and a* values of said almond when said discriminative model is a combination of the L* and a* values of each member of a population comprising bitter almonds and non-bitter almonds, wherein said combination discriminates between the sub-population of bitter almonds and the sub-population of non-bitter almonds in said population, wherein bitter almonds are assigned to a range Ra1 of said combination and non-bitter almonds are assigned to a range Ra2 of said combination; or a value Vb from the discriminative model using the L* and b* values of said almond, when said discriminative model is a combination of the L* and b* values of each member of said population, wherein said combination discriminates between the sub-population of bitter almonds and the sub-population of non-bitter almonds in said population, wherein bitter almonds are assigned to a range Rb1 of said combination and non-bitter almonds are assigned to a range Rb2 of said combination; and stage (e) classifies the almond using the value Va or Vb obtained according to the discriminative model of stage (d), wherein said almond is classified as a bitter almond when:

Va falls inside range Ra1;
Va falls outside range Ra2;
Vb falls inside range Rb1; or
Vb falls outside range Rb2.

6. The procedure for the detection of bitter almonds according to claim 5,
wherein
said discriminative model is developed by:
(I) performing stages (a) to (c) for each almond in said population comprising bitter almonds and non-bitter almonds;
(II) segmenting each image acquired for each almond in said population into RGB channels and obtaining the average RGB values over all pixels of each image;
(III) transforming the average RGB values of each image acquired for each almond in said population into the corresponding CIE L*a*b* values;
(IV) calculating a combination of:
the L* and a* values of each almond in said population; or
the L* and b* values of each almond in said population
wherein each combination discriminates between the sub-population of bitter almonds and the sub-population of non-bitter almonds in said population.

7. The procedure for the detection of bitter almonds according to claim 6, which additionally comprises the following stage after stage (III) and before stage (IV) of performing multivariate data analysis by linear discriminant analysis which obtains:
a discriminant function when using the R, G and B parameters of each almond in said population; or
a discriminant function when using L*, a* and b* parameters of each almond in said population,
wherein:
the value of the discriminant function determined using the R, G and/or B parameters of each almond in said population; or
the value of the discriminant function determined using the L*, a* and/or b* parameters of each almond in said population discriminates between the sub-population of bitter almonds and the sub-population of non-bitter almonds in said population.

8. The procedure for the detection of bitter almonds according to claim 1, wherein stage (c) comprises acquiring an image of multiple almonds, wherein each image of each almond is separated therefrom by image recognition software.

9. A device for carrying out the procedure of claim 1, wherein said device comprises at least:
a cell where the sample to be analyzed is placed according to step (a);
a UV light radiation system with at least one source of UV light configured to carry out step (b);
a positioned photographic camera which photographs the sample according to step (c) for subsequent analysis by means of a computer system; and the computer system is configured to preform classification of the sample into sweet and bitter almonds depending on a result obtained upon applying a discriminative model according to steps (d) and (e).

10. The device for the detection of bitter almonds according to claim 9, wherein the UV light radiation system comprises a source of UV light that is applied with wavelengths<400 nm at a distance of between 0.1 m and 1 m between the light source and the sample.

11. The device for the detection of bitter almonds according to claim 9, wherein the computer system comprises a computer programme which controls and processes the detection of the bitter almonds.

12. A system for the detection of bitter almonds, which comprises the following:
(a) means for placing at least one almond on a surface by means of a manual or automatic supply system;
(b) means for illuminating the almond with a source of ultraviolet (UV) radiation;
(c) means for acquiring an image of the almond with a photographic camera and storing said image in an internal or external system for subsequent analysis;
(d) means for processing said acquired image with a computer system that comprises a programme for applying a discriminative model;
(e) means for classifying the almond as bitter or non-bitter according to said discriminative model; and
(f) means for withdrawing the almond by means of a manual or automatic withdrawal system,
wherein (d) in turn comprises the following:
i. means for processing the data of the acquired image and segmentation of the image to establish the RGB colour parameters of a sample;
ii. means for transforming the RGB colour parameters obtained in stage i into at least one L*a*b* parameter of the CIE L*a*b* space;
iii. means for determining at least one of the L*, a* and/or b* parameters of the CIE L*a*b* space and its corresponding value in said image; and
iv. means for interpolating the value obtained by iii in said discriminative model generated from the values obtained with different sample types of bitter and non-bitter almonds acquired under predetermined conditions.

13. The system for the detection of bitter almonds according to claim 12, wherein in (a), the sample is placed in a closed cell without penetration of sunlight.

14. The system for the detection of bitter almonds according to claim 12, wherein the illumination of a cell is carried out with UV radiation having wavelengths<400 nm at a distance between the light source and the sample of between 0.1 m and 1 m.

15. The system for the detection of bitter almonds according to claim 12, wherein the photography of the sample is performed at a distance between the camera and the sample of between 0.1 m and 1 m, under conditions of the absence of sunlight and application of UV radiation.

16. The system for the detection of bitter almonds according to claim 12, wherein: said almond is a skinned almond; the processing of (d) in turn comprises the following:
  (i) segmenting the image into RGB channels and obtaining the average RGB values over all pixels of said image;
  (ii) transforming the average RGB values into the corresponding CIE L*a*b* values;
  (iii) interpolating:
  a value Va from the discriminative model using the L* and a* values of said almond when said discriminative model is a combination of the L* and a* values of each member of a population comprising bitter almonds and non-bitter almonds, wherein said combination discriminates between the sub-population of bitter almonds and the sub-population of non-bitter almonds in said population, wherein bitter almonds are assigned to a range Ra1 of said combination and non-bitter almonds are assigned to a range Ra2 of said combination; or
  a value Vb from the discriminative model using the L* and b* values of said almond, when said discriminative model is a combination of the L* and b* values of each member of said population, wherein said combination discriminates between the sub-population of bitter almonds and the sub-population of non-bitter almonds in said population, wherein bitter almonds are assigned to a range Rb1 of said combination and non-bitter almonds are assigned to a range Rb2 of said combination; and
  (e) classifies the almond using the value Va or Vb obtained according to the discriminative model of (d), wherein said almond is classified as a bitter almond when:
  Va falls inside range Ra1;
  Va falls outside range Ra2;
  Vb falls inside range Rb1; or
  Vb falls outside range Rb2.

17. The system for the detection of bitter almonds according to claim 16, wherein said discriminative model is developed by:
  (I) means for performing (a) to (c) for each almond in said population comprising bitter almonds and non-bitter almonds;
  (II) means for segmenting each image acquired for each almond in said population into RGB channels and obtaining the average RGB values over all pixels of each image;
  (III) means for transforming the average RGB values of each image acquired for each almond in said population into the corresponding CIE L*a*b* values;
  (IV) means for calculating a combination of:
  the L* and a* values of each almond in said population; or
  the L* and b* values of each almond in said population wherein each combination discriminates between the sub-population of bitter almonds and the sub-population of non-bitter almonds in said population.

18. The system for the detection of bitter almonds according to claim 17, which, after transforming using (III) and before calculating using (IV), additionally comprises performing multivariate data analysis by linear discriminant analysis which obtains:
  a discriminant function when using the R, G and B parameters of each almond in said population; or
  a discriminant function when using L*, a* and b* parameters of each almond in said population,
  wherein:
  the value of the discriminant function determined using the R, G and/or B parameters of each almond in said population; or
  the value of the discriminant function determined using the L*, a* and/or b* parameters of each almond in said population discriminates between the sub-population of bitter almonds and the sub-population of non-bitter almonds in said population.

19. The system for the detection of bitter almonds according to claim 12, wherein (c) comprises means for acquiring an image of multiple almonds, wherein each image of each almond is separated therefrom by image recognition software.

20. The system for the detection of bitter almonds according to claim 12, wherein:
  the means for placing at least one skinned almond on a surface comprises a manual or automatic supply or dispensing means;
  the means for illuminating the almond with a source of ultraviolet (UV) radiation comprises a cell where the sample to be analysed is positioned and a UV light radiation system with at least one source of UV light;
  the means for acquiring an image of the almond comprises a positioned photographic camera which photographs the sample for subsequent analysis by means of the computer system; and
  the means for processing said acquired image comprises a computer system which comprises a programme for applying a discriminative model for classification of the sample into sweet and bitter almonds depending on a result obtained upon applying the discriminative model.

* * * * *